United States Patent [19]
Maxwell, III et al.

[11] Patent Number: 5,945,342
[45] Date of Patent: Aug. 31, 1999

[54] METHOD FOR DIGESTING SPENT ION EXCHANGE RESINS AND RECOVERING ACTINIDES THEREFROM USING MICROWAVE RADIATION

[75] Inventors: Sherrod L. Maxwell, III, Aiken, S.C.; Sheldon T. Nichols, Augusta, Ga.

[73] Assignee: Westinghouse Savannah River Company, Aiken, S.C.

[21] Appl. No.: 09/080,595

[22] Filed: May 18, 1998

[51] Int. Cl.[6] .............. G01N 33/20; G01N 1/00; G01N 30/02; C22B 59/00
[52] U.S. Cl. .............. 436/81; 423/7; 423/20; 423/21.1; 423/21.5; 423/63; 423/68; 423/53; 423/54; 423/49; 423/139; 423/100; 423/109; 423/89; 423/98; 436/82; 436/83; 436/84; 436/161; 436/175; 204/157.43
[58] Field of Search ............... 423/7, 20, 21.1, 423/21.5, 63, 68, 53, 54, 49, 139, 150.1, 100, 109, 89, 98; 204/157.43; 436/82, 83, 84, 81, 161, 175; 422/70

[56] References Cited

U.S. PATENT DOCUMENTS

| | | | |
|---|---|---|---|
| 3,629,135 | 12/1971 | Wilding | 252/301.1 |
| 3,669,631 | 6/1972 | Dietrich et al. | 23/342 |
| 4,203,952 | 5/1980 | Hancock et al. | 423/6 |
| 4,351,643 | 9/1982 | Govindaraju | 23/230 |
| 4,687,581 | 8/1987 | Macedo et al. | 210/670 |
| 4,718,358 | 1/1988 | Nomi et al. | 110/250 |
| 4,800,024 | 1/1989 | Elfline | 210/665 |
| 4,835,107 | 5/1989 | Horwitz et al. | 436/82 |
| 4,935,114 | 6/1990 | Varma | 204/157.43 |
| 4,968,504 | 11/1990 | Rourke | 423/7 |
| 5,078,842 | 1/1992 | Wood et al. | 204/1.5 |
| 5,126,272 | 6/1992 | Kingston, Jr. et al. | 436/77 |
| 5,130,001 | 7/1992 | Snyder et al. | 204/157.2 |
| 5,190,881 | 3/1993 | McKibbin | 436/82 |
| 5,281,631 | 1/1994 | Horwitz et al. | 521/38 |
| 5,420,039 | 5/1995 | Renoe et al. | 436/175 |
| 5,449,462 | 9/1995 | Horwitz et al. | 210/682 |
| 5,476,989 | 12/1995 | Mimori et al. | 588/20 |
| 5,505,925 | 4/1996 | Fristad | 423/1 |
| 5,523,514 | 6/1996 | Cauquil et al. | 588/20 |
| 5,835,866 | 11/1998 | Bridges et al. | 588/19 |
| 5,840,583 | 11/1998 | Barclay | 436/81 |

FOREIGN PATENT DOCUMENTS

| | | |
|---|---|---|
| 0 462 353 | 12/1991 | European Pat. Off. . |
| 56-168025 | 12/1981 | Japan . |
| 61-153308 | 7/1986 | Japan . |

OTHER PUBLICATIONS

Zschunke, et al, "Separation of actinides of dissolved radioactive waste" Schr. Forschungszent. Juelich, Reihe Energietech./Energy Technol., pp. 337–340, 1998.

*Primary Examiner*—Steven Bos
*Attorney, Agent, or Firm*—Kilpatrick Stockton LLP; Dean W. Russell; Bruce D. Gray

[57] ABSTRACT

The present invention relates to methods for digesting diphosphonic acid substituted cation exchange resins that have become loaded with actinides, rare earth metals, or heavy metals, in a way that allows for downstream chromatographic analysis of the adsorbed species without damage to or inadequate elution from the downstream chromatographic resins. The methods of the present invention involve contacting the loaded diphosphonic acid resin with concentrated oxidizing acid in a closed vessel, and irradiating this mixture with microwave radiation. This efficiently increases the temperature of the mixture to a level suitable for digestion of the resin without the use of dehydrating acids that can damage downstream analytical resins. In order to ensure more complete digestion, the irradiated mixture can be mixed with hydrogen peroxide or other oxidant, and reirradiated with microwave radiation.

14 Claims, No Drawings

METHOD FOR DIGESTING SPENT ION EXCHANGE RESINS AND RECOVERING ACTINIDES THEREFROM USING MICROWAVE RADIATION

BACKGROUND OF THE INVENTION

1. Field of the Invention

This invention relates to the digestion and disposal of spent ion exchange resins and the recovery of actinide, rare earth metal, and/or heavy metal species from these resins. More particularly, the invention relates to the digestion of actinide, rare earth metal, or heavy metal loaded ion exchange resins in such a way that these species can be subsequently analyzed without interference from the resin digestion products, thereby allowing an accurate analytical assessment of the identity and amount of these materials loaded in the resins.

2. Description of the Related Art

Ion exchange resins are widely used to clean up waste and cooling water from the nuclear power and nuclear weapons industries, and in particular to remove radioactive, rare earth metal, and/or heavy metal species from the water so that the water can be reused or disposed of as a lower level waste product. However, these ion exchange resins eventually become fully loaded with the metal species, and cease to perform their function effectively. When this happens, the resin must be replaced, and the spent, loaded resin presents another disposal problem. Various methods exist for disposing of the spent resin, including digestion of the organic constituents to decrease the resin volume and/or immobilization of the remaining radioactive or hazardous species in some final form, such as ceramic or glass, that is stable, low in volume, and relatively easy and safe for handling and disposal.

Ion exchange resins suitable for waste water treatment may be of a number of different types, including those having diphosphonic acid and/or sulfonic acid groups on a polymer backbone. In particular, resins having polystyrene-containing backbones that have been crosslinked with divinylbenzene and substituted with diphosphonic and/or sulfonic acid substituent groups have been found to be particularly suitable in this regard. Resins having diphosphonic acid substituent groups have been found to be particularly suitable because of the efficiency and tenacity with which the these moieties bind cations, including cations of radioactive species, namely actinide cations, as well as rare earth metal cations, and heavy metal cations. DIPHONIX resin (diphosphonic and/or sulfonic acid substituted polystyrene/divinylbenzene resin, Eichrom Industries, Inc.) is particularly effective in removing actinides from wastewater, and from large soil samples. Suitable diphosphonic acid containing resins are disclosed in U.S. Pat. Nos. 5,281,631 and 5,449,462, the entire contents of which are hereby incorporated by reference.

In many cases, it is desirable to analyze the amount and identity of actinides, rare earths, or heavy metal loaded on the resin in order to obtain information useful to assess and control the upstream nuclear processes. It is also often desirable to analytically and quantitatively assess the level of radioactive species, such as actinides, or hazardous metal species, such as rare earth or heavy metals, in samples of water, bodily fluids, soil, fecal samples, etc., in order to assess the level of exposure of the environment or individuals to these potentially harmful species, as well as to determine a suitable disposal method for these materials.

While it would be desirable to do this using the diphosphonic acid substituted ion exchange resins discussed above (because of their effectiveness and efficiency in capturing these species), this is made very difficult by the very tenacity of the resins for actinides, rare earth metal, and heavy metal cations that make them so effective in the first place. In short, it is very difficult to elute the actinide, rare earth metal, or heavy metal cations from the loaded resin in any significant amounts. Destruction of these removal resins by digestion of the organics is also difficult, because if the resin is not completely destroyed, then organic residual groups containing phosphonic acid moieties can rebind to the metal species. When this occurs, the phosphonic acid/metal bound complex can then become bound to the chromatographic or analytical resins used in the downstream analytical processes. This bonding is sufficiently strong that it can cause substantial difficulties in eluting the actinides from the downstream analytical resins for further analysis. Diphosphonic acid-substituted resins, such as DIPHONIX, are particularly troublesome in this regard.

U.S. Pat. No. 5,523,514 discloses low temperature digestion of plutonium-contaminated ion exchange resins, such as DOWEX, with sulfuric acid in an open microwave vessel. However, nitric acid was not found to work with these resins in this process, as indicated by the Table disclosed in the '514 patent. Diphosphonic acid-substituted resins are even more difficult to digest than DOWEX, and cannot be effectively digested using low temperature nitric acid processes. Further, sulfuric acid is unsuitable for digestion in a closed microwave reaction vessel because the sulfuric acid will attack the vessel lining at the elevated temperatures and pressures achieved in a closed vessel. In addition, digestion of the actinide-loaded removal resin with some strong acids, in particular sulfuric acid, is detrimental to the downstream analytical separation processes, in particular downstream separations using column chromatography.

As a result, there exists a need for a method of processing removal resins loaded with actinides, rare earth metals, and/or heavy metals, and in particular a method of processing diphosphonic acid substituted resins loaded with one or more of these materials, in a way that allows the use of downstream analytical resins without undue difficulty in eluting the actinides or rare earth metals, and without damage to downstream analytical resins. It is one object of the present invention to provide such a process.

More specifically, it is an object of the invention to provide a process capable of fully digesting a diphosphonic acid-substituted ion exchange resin.

It is also an object of the present invention to release actinides, rare earth metal, and/or heavy metal cations from a diphosphonic acid-substituted ion exchange resin in a manner that allows accurate analysis of the type and quantity of these cations by subsequent chromatographic processes.

It is also an object of the present invention to provide a digestion step for diphosphonic acid substituted cation exchange resins that will not damage chromatographic resins used in downstream analytical processes.

SUMMARY OF THE INVENTION

These and other objectives are achieved by the presently claimed invention, which is directed to a method of digesting one or more diphosphonic acid substituted resins that have been loaded with actinide, rare earth metal, or heavy metal cations by contacting the loaded resin with a low boiling point oxidizing acid, such as nitric acid, in a closed microwave reaction vessel, and irradiating this mixture with microwave radiation. The radiation is maintained for a sufficient time and at a sufficient energy that some or all of the loaded resin is digested by the acid. Additional steps that may be used to further increase digestion efficiency include cooling the digested mixture obtained above, adding hydrogen peroxide to the mixture, and reirradiating this mixture with additional microwave radiation to ensure complete digestion of any remaining organic components in the product.

The present invention is also directed to a method for determining the identity and concentration of actinides, rare earth, or heavy metal elements in a sample by (1) dissolving or diluting the sample in water to form a sample solution;
(2) contacting the sample solution with a diphosphonic acid-substituted ion exchange resin under conditions sufficient to adsorb actinides, rare earth metals, and heavy metals thereon;
(3) removing the diphosphonic acid-substituted ion exchange resin from contact with the sample solution;
(4) releasing the actinide, rare earth, or heavy metal elements from the diphosphonic acid-substituted ion exchange resin according to the method described above to form a digested residue;
(5) analyzing the actinide, rare earth, or heavy metal content of the digested residue by column chromatography.

The methods of the present invention remove actinide, rare earth, and heavy metal cations from diphosphonic acid containing resins without damaging either the reaction vessel used to digest the resin or downstream analytical chromatographic resins, or causing elution problems with analytical resins used for downstream column chromatography. The present invention therefore provides a method for accurately determining the identity and quantity of actinide, rare earth, and/or heavy metals in a sample when highly efficient removal resins are used to adsorb these metals from a sample, or from contaminated wastewater. The method of the present invention thus utilize high temperature and high pressure digestion conditions that are suitable to digest very resistant, difficult to digest resins without the use of dehydrating acids that become problematic for downstream processing.

The present invention can be more clearly understood by reference to the following Detailed Description of Specific Embodiments, which is not intended to limit the scope of the appended claims.

DETAILED DESCRIPTION OF SPECIFIC EMBODIMENTS

While the process of the present invention can be used with a wide variety of ion exchange resins, it is particularly suitable for use with cation exchange resins that are difficult to digest with conventional methods. In particular, the invention has been found to be suitable for use with diphosphonic acid substituted resins, such as DIPHONIX, produced by Eichrom Industries, Inc., and described in U.S. Pat. Nos. 5,281,631 and 5,449,462. DIPHONIX resins typically are prepared by copolymerizing a vinylidene diphosphonic acid with styrene or similar unsaturated monomer, acrylonitrile or similar (meth)acrylate, and divinylbenzene (as a crosslinking agent). In its commercial form, DIPHONIX is a multifunctional chelating gel form cation exchange resin containing geminally substituted diphosphonic acid ligands chemically bonded to a polystyrene-based matrix. DIPHONIX is typically sold in two mesh sizes: 50–100 mesh and 100–200 mesh. The methods of the present invention will work on resin particles of any size, and will work with either industrial grade resin, such as that sold to copper mining plants, etc., or analytical grade resin, sold to laboratories. The use of DIPHONIX resins per se to remove heavy metals, rare earth metals, and actinides from solution is known in the art, and the DIPHONIX resins are desirably used in their hydrogen ion form, but may also be in a form having a different cation adsorbed thereon, such as calcium ion. Typically, the resin is first conditioned by contacting it with an acid solution of the same type as is used to acidify the sample or material containing the actinides, rare earths, or heavy metals. For instance, a mixture of hydrochloric acid and hydrofluoric acid (e.g., in a 1.75:1 molar ratio) may be used to redissolve or acidify a sample to be contacted with the diphosphonic acid resin. The resin can be first rinsed with this mixture to condition it for adsorption, then contacted with the sample, then rinsed with a mixture or hydrochloric and hydrofluoric acid (e.g., from about a 3:1 molar ratio to about a 1:1 molar ratio, more particularly a 1:1 molar ratio), then with water. Of course, other acids and acid mixtures may be used to acidify or redissolve the sample or to condition the resin, and the acids or acid mixture used to prepare the sample need not be the same as that used to condition the resin.

The methods of the present invention are useful to digest diphosphonic acid substituted ion exchange resins that have been loaded with actinides, such as Th, Pa, U, Np, Pu, Am, Cm, Bk, Cf, Es, Fm, Md, No, and Lr, more particularly Pu, Am, U, Th, and Np, typically in the +2, +3, +4, +5, or +6 oxidation states. Alternatively or additionally, the resins may be loaded with rare earth elements, such as La, Ce, Pr, Nd, Pm, Sm, Eu, Gd, Tb, Dy, Ho, Er, Tm, Yb, Lu, typically in the +2, +3, or +4 oxidation states. Resins loaded with heavy metals, such as V, Cr, Mn, Co, Ni, Zn, Cd, Hg, Pb, and Fe may also be digested using the method of the present invention. Resins loaded with combinations of actinides, rare earths, and heavy metals can be digested according to this method as well, and the terminology "actinides, rare earths, and/or heavy metals" and "actinides, rare earths, or heavy metals" and similar terminology should be interpreted to include combinations of the components.

With respect to the use of the process to digest resins loaded in whole or in part with heavy metals, quantitative recovery of these species may require using a system for dissolving any samples that is different from that used with actinides. However, the HCl-HF system used to dissolve samples for actinide analysis will allow accurate measurement of heavy metals loaded on the resin. Moreover, some heavy metals (not including iron) can be eluted from diphosphonic acid containing resins without digestion. Accordingly, the main application of the present invention to analysis of resins containing heavy metals is with a combination of heavy metal and actinide loading, such as in wastewater cleanup resins.

The loaded resin is contacted with a low boiling point oxidizing acid in a closed pressure type reaction vessel. Typically, this low boiling point oxidizing acid is nitric acid. However, a mixture of nitric acid and hydrochloric acid, such as aqua regia, could be used. Nitric acid will not create elution problems with or damage downstream chromatography resins, and is also an acid that may be used to create an acidic medium for adsorption of the metal species onto the diphosphonic acid substituted resin. Concentrated (70 wt %) $HNO_3$ is typically used, having a concentration of about 15.7N, however nitric acids in a concentration of about 12 to about 16 N may be used. Dehydrating acids, such as sulfuric acid, are generally not suitable for the methods of the present invention. These acids can damage downstream analytical chromatography resins, and can damage the reaction equipment itself at the elevated temperatures and pressures achieved with microwave heating in a closed vessel used in the present invention.

The amount of resin treated in the process is in part governed by the pressure limitations on the reaction vessels. In vessels limited to pressures of around 625 psi, the process is typically conducted with about 1.0 to about 3.0 ml of resin, in order to allow for an adequate safety margin where the operating pressure is no greater than about 550 psi. However, the use of reaction vessels capable of withstanding higher pressure, such as vessels capable of withstanding about 1000 psi or more, can allow the use of the process with anywhere from about 1 ml to about 30 ml of resin. The nitric acid is typically added in an amount of about 7 ml to about 20 ml of concentrated nitric acid (15.7 N) per 3 ml of loaded resin, more particularly an amount of about 10 ml concentrated nitric acid per 3 ml of loaded resin. In order to use resin amounts of about 2.8 ml to about 3 ml, a predigestion step may be employed in order to avoid overpressurization of the reaction vessel. In this step, the resin and acid are heated using microwave radiation to a temperature of about 190° C. for 15–20 minutes. The temperature is generally ramped by linearly increased from room temperature to about 190° C. over about 4 to about 7 minutes, with a longer time period for a larger quantity of material. The mixture is cooled, and the reaction vessel vented to relieve pressure. The main digestion step is then performed by heating to a temperature of about 220° C. to about 225° C. for about 35 minutes. The temperature is generally ramped by linearly increased from either room temperature, or if a predigestion step is used, from the temperature at which venting occurs, over a period of about 4 to about 8 minutes, again depending upon the amount of material to be digested, with more material increasing the ramp time.

As indicated above, pressure in the reaction vessel may be monitored directly (along with temperature) and controlled indirectly by controlling the temperature of the mixture, and the amount of resin charged to the reactor. Typical digestion temperatures are in the range from about 170° C. to about 250° C., typically around 220° C. This can lead to superatmospheric pressures in a closed system on the order of about 500 psig to over 1,000 psig, typically around 550 psig, depending on the amount of resin charged, as discussed above. The pressure vessel used should be capable of safely withstanding pressures in the range that will be attained at the temperature and resin charge used, allowing for an adequate safety margin, and should be suitable for efficiently transmitting received microwave radiation to the reaction mixture. In a vessel capable of withstanding 625 psi, an operating pressure of about 550 psi is used to maintain an adequate safety margin. Suitable pressure vessels include standard commercial closed vessel microwave vessels, such as the QUESTRON Q WAVE 3000. These typically include TEFLON PFA because this material is transparent to microwave radiation, has excellent acid resistance, and a fairly high melting point.

The microwave radiation used to heat the mixture of acid and resin typically has a wavelength in the range from about 1 mm to about 1 m, typically around 12 cm. The frequency of the microwave radiation is typically from about 0.3 to about 300 Ghz, typically around 2.45 Ghz. The microwave radiation is typically provided at a power of from about 0.1 kW to about 10 kW, typically about 1 kW to the mixture. This irradiation is typically maintained for a period of about 10 to 40 minutes, typically about 35 minutes. The microwave radiation can be supplied by any suitable means, for example by direct coupling of a magnetron or microwave generator to the reaction vessel, or by transmission of microwaves to the reaction vessel by a waveguide from a magnetron or microwave generator located at a distance from the reaction vessel. Suitable magnetrons or microwave generators include the QUESTRON Q WAVE 3000, but other manufacturers and models of microwave equipment may be used, provided that they provide the power and frequency of microwaves described above. Because of the aqueous nature of the reaction system, it is not necessary to use a high efficiency microwave cavity.

While not wishing to be bound by any theory, it is believed that the microwave radiation quickly heats the mixture of acid and loaded resin, in part due to the dipole relaxation spectra of the water in the aqueous system, leading to intense microwave absorption. The high frequency electric field applied by the microwave radiation polarizes charges in the reaction mixture materials, which cannot maintain their polarization in phase with the rapid reversals of the field. The resulting high temperature and pressure that occur in the closed reaction vessel provide the conditions necessary to digest the resin with nitric acid. The use of microwaves to heat the mixture also provides a measure of "tunability," allowing the microwave absorption of the mixture to be varied and maximized with temperature, e.g., by varying the dimensions of the microwave cavity. Microwave heating is also characterized by high thermal and field intensity gradients, which cause agitation and mixing in the reaction mixture, which enhance homogenization and diffusion of the reaction mixture.

In order to further maximize the level of digestion, the digested mixture resulting from microwave heating in the presence of nitric acid may be further treated by cooling to a temperature that allows the microwave pressure vessel to be safely opened, typically below about 90° C., adding an oxidizer, such as hydrogen peroxide or potassium permanganate, more particularly hydrogen peroxide because it decomposes to water after reaction, to that described above and again subjecting the mixture to microwave radiation of similar duration and intensity to that described above, in order to ensure full digestion of the resin and any organic digestion products. Typically, a 30 wt % solution of hydrogen peroxide can be added in an amount of from about 0.3 ml to about 10 ml, more particularly about 3.5 ml, per 3 ml of original loaded resin. The additional microwave irradiation is carried out at a sufficient energy to raise the temperature of the mixture to between 170 and 250° C., typically around 210° C., for about 5 to about 40 minutes, typically about 15 minutes. The temperature is generally ramped by linearly increasing to the heating temperature over a period of about 10 minutes.

Again, not wishing to be bound by any theory, it is believed that microwave heating of the loaded resin in the presence of nitric acid oxidizes the resin polymer to carbon dioxide, phenyl compounds, benzene, etc. and detaches the diphosphonic acid moieties from the polymer backbone. Some or all of these acid moieties may be oxidized to phosphates. Addition of hydrogen peroxide or other oxidizing agent, together with another course of microwave heating, is believed to help break apart diphenyl rings that may have survived the first oxidation, and helps to clear the digestion medium, achieving a more complete oxidation.

The digestion method of the present invention allows assessment of the efficiency of diphosphonic acid substituted resins whose primary purpose is to remove actinides, rare earths, and/or heavy metals from wastewater. The method may also form a part of an overall method for analyzing the type and amounts of metal ions present in a sample. Such an overall method would comprise dissolving a sample believed to be contaminated with, e.g., actinides, in water using a strong acid. This sample is then contacted with a diphosphonic acid substituted cation exchange resin, such as DIPHONIX, in order to remove the actinides from the sample onto the removal resin. The removal resin is then digested using the methods of the present invention, and the fully digested resin analyzed using column chromatography as described, e.g., in U.S. Pat. No. 4,835,107, the entire contents of which is hereby incorporated by reference. The actinides can then be eluted and analyzed by alpha counting or other appropriate techniques known to those of skill in the art.

The digested resin/metal mixture may be adjusted to an appropriate nitric acid concentration for subsequent analysis. For direct analysis on an instrument, almost any nitric acid concentration is suitable, and dilution or adjustment may not be required. For column chromatography to determine the presence and amount of actinides, the mixture is typically adjusted to 2.5 M nitric acid. This is typically done by evaporating to remove the acid and adding small amount (about 1 ml of 30 wt % per 3 ml of original loaded resin) of hydrogen peroxide. This mixture is then typically redissolved in a small volume, typically 7–8 ml, based on 3 ml of original loaded resin, of 5 M nitric acid. If necessary, aluminum nitrate can be added to complex interfering phosphate ions in order to assist in preventing any interference with subsequent chromatography separations. This is typically done by adding about 5 ml of a 2 M aluminum nitrate solution and 2 ml of water or 0.1 M nitric acid. The resulting solution is typically about 0.75 M in aluminum nitrate and about 2.5 M in nitric acid.

The invention can be more clearly understood by reference to the following examples, which are illustrative and not limiting of the invention. The goal for actinide radiochemistry with respect to large soil samples is to obtain relatively high chemical yields or recoveries, so that radiochemical tracers can be accurately measured. This allows yield corrections to be applied to the actinides measured in the soil sample. The examples below show that relatively high chemical yield or recoveries are obtained using this method when applied to large soil samples (i.e., greater than 80% recovery of spiked standards). Since the actinide elements are retained much more strongly than most other metal ions on the DIPHONIX resin, data showing that the actinide elements can be recovered successfully indirectly indicates that rare earth and heavy metal ions can also be recovered.

EXAMPLES

Example 1

In order to assess the ability of the process to recover actinides from DIPHONIX resin, a series of tests were carried out using five standard solutions of uranium, two soil samples spiked with 2000 ng of uranium, and two unspiked soil samples.

Five gram soil samples, both spiked and unspiked, were leached at 180° C. in 1.75 M HCl-1M HF using a microwave digestion method for 15 minutes. After filtering, the leachate was evaporated to dryness and redissolved in a mixture of 1.75 M HCl and 1 M HF. The mixture was contacted with 1 ml of DIPHONIX resin, which was then digested with 7 ml of concentrated nitric acid (15.7 M). The digestion mixture was heated to a temperature of 220° C. with microwave radiation having a frequency of 2.45 GHz for a period of 35 minutes. This mixture was then filtered a UTEVA resin (diamylphosphonate on an inert support, Eichrom Industries, Inc.). ICP-MS was used to measure uranium in the digest before and after UTEVA column separation. The results are presented in Table 1, below. Agreement between uranium measured directly and after UTEVA separation (i.e., high % recovery) indicates complete digestion of the DIPHONIX resin, since incomplete digestion would result in uranium-DIPHONIX residue would filter out on the UTEVA resin. A similar procedure was carried out with the standard solutions, except that these were dissolved and contacted with the DIPHONIX resin without the leaching steps used for the soil samples.

TABLE 1

| SAMPLE | DIRECT ASSAY ppb | AFTER UTEVA ppb | % RECOVERY UTEVA/DIRECT ASSAY |
|---|---|---|---|
| Std 1 | 85 | 74 | 87 |
| Std 2 | 85 | 77 | 91 |
| Std 3 | 83 | 85 | 102 |
| Std 4 | 78 | 81 | 104 |
| Std 5 | 81 | 80 | 99 |
| Avg Std. | 82 | 79 | 97 |
| Spiked Soil 1 | 227 | 183 | 81 |
| Spiked Soil 2 | 233 | 235 | 101 |
| Blank Soil 1 | 117 | 113 | 97 |
| Blank Soil 2 | 174 | 163 | 94 |
| Avg | | | 93 |

Example 2

Leachates similar to those described in Example 1 were prepared with larger spiked and unspiked soil samples. 10 g and 15 g soil leachates were combined to prepare the 50 g and 60 g sample leachates. These were filtered and evaporated to dryness and redissolved in 1.5 M HCl-1M HF. Samples were adjusted to be 0.5 M in ascorbic acid to reduce iron, but EDTA was not added. The samples were contacted with approximately 2 ml of DIPHONIX resin in two separate cartridges stacked in tandem. The resin in the cartridges was digested as described in Example 1. The uranium present in the digest was then analyzed by ICP-MS. The results are presented in Table 2 below.

TABLE 2

| SAMPLE | URANIUM MEASURED mg | URANIUM ADDED mg | URANIUM PREDICTED mg | % RECOVERY OF PREDICTED |
|---|---|---|---|---|
| 15 g unspiked | 0.0188 | 0 | — | — |
| 15 g 2d cartridge | 0.0000 | — | — | — |
| 50 g unspiked (calculated) | 0.0625 | 0 | — | — |
| 50 g spiked | 0.1460 | 0.09975 | 0.1623 | 90 |
| 50 g spiked 2d cartridge | 0.0218 | — | — | 13 |
| 60 g unspiked (calculated) | 0.0750 | — | — | — |
| 60 g spiked | 0.1820 | 0.120 | 0.195 | 93 |
| 60 g spiked 2d cartridge | 0.0168 | — | — | 9 |

No uranium was detected in the second cartridge of resin for the fifteen gram unspiked soil sample. The unspiked value of 0.0188 mg was therefore taken as the amount of uranium leached from a 15 g sample. Unspiked values were calculated for larger sample sizes based on the 15 g unspiked sample. In the second cartridges for the 50 g and 60 g spiked samples, 13% and 9%, respectively of the total uranium predicted were measured respectively. This agreed well with the amount of uranium that apparently passed through the first columns. The use of a second column extends the range of the method significantly. However, two microwave vessels are required per sample.

Example 3

A procedure similar to that of Example 2, but with soil that was unspiked and spiked with thorium. The results appear in Table 3. The unspiked value of 0.0644 mg was taken as the amount of thorium leached from a 10 g sample.

TABLE 3

| SAMPLE | THORIUM MEASURED mg | THORIUM ADDED mg | THORIUM PREDICTED mg | % RECOVERY |
|---|---|---|---|---|
| 10 g unspiked | 0.0644 | 0 | — | — |
| 20 g unspiked (calculated) | 0.1288 | — | — | — |
| 20 g spiked | 0.1540 | 0.040 | 0.1688 | 91 |
| 20 g spiked | 0.1694 | 0.040 | 0.1688 | 100 |
| 30 g unspiked (calculated) | 0.1932 | — | — | — |
| 30 g spiked | 0.2440 | 0.090 | 0.2832 | 86 |
| 50 g unspiked (calculated) | 0.3220 | — | — | — |
| 50 g spiked | 0.3880 | 0.150 | 0.4720 | 82 |
| 50 g spiked | 0.4360 | 0.150 | 0.4720 | 92 |
| 50 g spiked 2d cartridge | 0.0168 | — | — | 4 |

Example 4

The amount of DIPHONIX resin was increased to approximately 2.8 ml to enhance recovery of trivalent actinides. A test procedure similar to that followed in Example 1 was used, except that the UTEVA resin was replaced by TEVA (Aliquat 336N acrylic ester nonionic polymeric adsorbent coated resin, Eichrom Industries, Inc.). Table 4 shows plutonium spike recovery data for soil samples of various sizes. A relatively high level of total plutonium spike of $3.05 * 10^5$ dpm was added to each sample to facilitate measurement using planchet mounting of both the DIPHONIX digest solution and plutonium after TEVA column separation. Spike recoveries for the assay of the digest solution before and after TEVA column purification are shown.

TABLE 4

| SAMPLE | DIRECT ASSAY dpm * $10^5$ | TEVA dpm * $10^5$ | % RECOVERY TEVA/DIRECT ASSAY |
|---|---|---|---|
| 10 g Pu spiked | 2.51 (82%) | 2.63 (86%) | 105 |
| 10 g Pu spiked | 2.81 (92%) | 2.84 (93%) | 101 |
| 10 g Pu spiked | 2.84 (93%) | 2.85 (93%) | 100 |
| Avg. spiked | 2.72 (89%) | 2.77 (91%) | 102 |

The average spike recovery of approximately 90% both before and after TEVA column purification demonstrates the effectiveness of the resin destruction technique and the high spike recovery that can be achieved using this method.

Example 5

Similar testing to that of Examples 1 and 4 was carried out using soil samples spiked with americium, and using TRU (polymeric resin coated with tri-n-butylphosphine and N,N-diisobutylcarbamoylmethylphosphine oxide) instead of UTEVA or TEVA. The results are shown in Table 5.

TABLE 5

| SAMPLE | DIRECT ASSAY dpm * $10^5$ | TRU dpm * $10^5$ | % RECOVERY |
|---|---|---|---|
| 10 g Am spiked | 1.63 (84%) | 1.64 (84%) | 100.6 |

The specific embodiments of the invention having herein been described, various modifications and variations thereof will become apparent to those of skill in the art. These modifications and variations are not intended to be excluded from the scope of the appended claims, or of equivalents thereto.

What is claimed is:

1. A method for releasing actinide, rare earth, or heavy metal elements from a diphosphonic acid-substituted ion exchange resin, comprising:
   (A) contacting a diphosphonic acid-substituted ion exchange resin having actinide, rare earth, or heavy metal elements adsorbed thereon with a low boiling point oxidizing acid in a closed microwave vessel to form a mixture; and
   (B) irradiating the mixture with microwave radiation for a sufficient time and at a sufficient energy, so that the mixture reaches a sufficient temperature to dissolve at least a portion of the resin to form a first digested mixture which releases the actinide, rare earth or heavy metal elements from the diphosphonic acid-substituted ion exchange resin.

2. The method according to claim 1, further comprising:
   (C) cooling the first digested mixture;
   (D) adding hydrogen peroxide to the first digested mixture to form a second mixture; and
   (E) irradiating the second mixture with microwave radiation for a sufficient time and at a sufficient temperature to dissolve at least a portion of the second mixture.

3. The method according to claim 1, wherein the low boiling point oxidizing acid is nitric acid.

4. The method according to claim 3, wherein the nitric acid has a normality of about 12 to about 16.

5. The method according to claim 1, wherein the temperature of the irradiated mixture is from about 170° C. to about 250° C.

6. The method according to claim 5, wherein the irradiation is carried out for a time between about 10 minutes and about 40 minutes.

7. The method according to claim 1, wherein the diphosphonic acid-substituted ion exchange resin comprises a polystyrene/divinylbenzene backbone substituted with diphosphonic acid groups.

8. The method according to claim 7, wherein the diphosphonic acid-substituted ion exchange resin is further substituted with sulfonic acid groups.

9. The method according to claim 2, wherein the hydrogen peroxide added has a concentration of about 30 wt %, based on the hydrogen peroxide composition.

10. A method for releasing actinide, rare earth, or heavy metal elements from a diphosphonic acid-substituted polystyrene/divinylbenzene ion exchange resin, comprising:
   (A) contacting a diphosphonic acid-substituted polystyrene/divinylbenzene ion exchange resin having actinide, rare earth, or heavy metal elements adsorbed thereon with nitric acid having a normality of about 12 to about 16 in a closed microwave vessel to form a mixture;

(B) irradiating the mixture with microwave radiation for about 10 minutes to about 40 minutes at an energy sufficient to obtain a mixture temperature of about 170° C. to about 250° C. and dissolving at least a portion of the resin to form a first digested mixture comprising organic digestion products;

(C) cooling the first digested mixture;

(D) adding hydrogen peroxide having a concentration of about 30 wt %, based on the hydrogen peroxide composition, to the first digested mixture to form a second mixture; and (E) irradiating the second mixture with microwave radiation for a sufficient time and at a sufficient temperature to digest said organic digestion products which releases the actinide, rare earth or heavy metal elements from the diphosphonic acid-substituted ion exchange resin.

11. A method for determining the identity and concentration of actinides, rare earth, or heavy metal cations present in a sample, comprising:

(1) dissolving or diluting the sample in water to form a sample solution;

(2) contacting the sample solution with a diphosphonic acid-substituted ion exchange resin under conditions sufficient to adsorb actinide, rare earth, or heavy metal cations thereon;

(3) removing the diphosphonic acid-substituted ion exchange resin from contact with the sample solution;

(4) releasing the actinide, rare earth, or heavy metal cations from the diphosphonic acid-substituted ion exchange resin;

by (A) contacting the diphosphonic acid-substituted ion exchange resin having actinide, rare earth, or heavy metal cations adsorbed thereon with a low boiling point oxidizing acid in a closed microwave vessel to form a mixture; and (B) irradiating the mixture with microwave radiation for a sufficient time and at a sufficient energy so that the mixture reaches a sufficient temperature to dissolve at least a portion of the resin to form a first digested mixture;

(5) analyzing the actinide, rare earth, or heavy metal content of the first digested mixture by column chromatography.

12. The method according to claim 11, wherein the sample is selected from the group consisting of a soil sample, a urine sample, a tissue sample, a fecal matter sample, a cooling water sample, and a wastewater sample.

13. The method according to claim 11, wherein the diphosphonic acid-substituted ion exchange resin comprises a diphosphonic acid-substituted polystyrene/divinylbenzene polymer that is optionally further substituted with sulfonic acid groups.

14. The method according to claim 13, wherein the releasing of the actinide, rare earth, or heavy metal cations in (4) comprises:

(A) contacting a diphosphonic acid-substituted polystyrene/divinylbenzene ion exchange resin having actinide, rare earth, or heavy metal cations adsorbed thereon with nitric acid having a normality of about 12 to about 16 in a closed microwave vessel to form a mixture;

(B) irradiating the mixture with microwave radiation for about 10 minutes to about 40 minutes at an energy sufficient to obtain a mixture temperature of about 170° C. to about 250° C. and dissolving at least a portion of the resin to form a first digested mixture comprising organic digestion products;

(C) cooling the first digested mixture;

(D) adding hydrogen peroxide having a concentration of about 30 wt %, based on the hydrogen peroxide composition, to the first digested mixture to form a second mixture; and (E) irradiating the second mixture with microwave radiation for a sufficient time and at a sufficient temperature to digest any remaining organic digestion products.

* * * * *